United States Patent
Holdgate et al.

(10) Patent No.: US 8,652,156 B2
(45) Date of Patent: Feb. 18, 2014

(54) SURGICAL INSTRUMENT (75) Inventors: James Alistair Holdgate, Cardiff (GB);
Hollie Elizabeth Johnston, Wiltshire (GB)

(73) Assignee: Gyrus Medical Limited, Cardiff (GB)

( * ) Notice: Subject to any disclaimer, the term of this patent is extended or adjusted under 35 U.S.C. 154(b) by 81 days.

(21) Appl. No.: 13/073,276

(22) Filed: Mar. 28, 2011

(65) Prior Publication Data
US 2011/0264129 A1    Oct. 27, 2011

(30) Foreign Application Priority Data
Mar. 31, 2010  (GB) .................................. 1005437.7

(51) Int. Cl.
*A61B 17/32*    (2006.01)
(52) U.S. Cl.
USPC .......................................................... 606/170
(58) Field of Classification Search
USPC ............... 606/1, 34, 39, 45, 46, 48, 128, 170, 606/176, 178–179, 180, 184, 205–208; 128/898; 604/167.03–167.06, 164.01, 604/164.02, 164.03, 164.08, 164.1
See application file for complete search history.

(56) References Cited

U.S. PATENT DOCUMENTS

| | | | | |
|---|---|---|---|---|
| 4,653,477 A | * | 3/1987 | Akui et al. ..................... | 600/154 |
| 4,715,360 A | * | 12/1987 | Akui et al. ..................... | 600/154 |
| 4,809,679 A | * | 3/1989 | Shimonaka et al. ........... | 600/154 |
| 5,104,383 A | * | 4/1992 | Shichman ................. | 604/167.06 |
| 5,263,944 A | * | 11/1993 | Vidal et al. ..................... | 604/256 |
| 5,338,307 A |   | 8/1994 | Stephens et al. | |
| 5,342,315 A | * | 8/1994 | Rowe et al. .............. | 604/167.06 |

(Continued)

FOREIGN PATENT DOCUMENTS

| | | |
|---|---|---|
| DE | 42 39 403 | 5/1994 |
| DE | 10 2009 012 205 | 9/2010 |

(Continued)

OTHER PUBLICATIONS

UK Search Report for GB Application No. 1005437.7, dated Jul. 28, 2010.

(Continued)

*Primary Examiner* — Ryan Severson
*Assistant Examiner* — David Eastwood
(74) *Attorney, Agent, or Firm* — Nixon & Vanderhye, PC (57) ABSTRACT

A morcellator (1) for morcellating tissue within a body cavity of a patient is provided in combination with first (17) and second (18) tissue-pulling devices, and an insert (19). The morcellator (1) comprises a handle portion (2) having a lumen (6) passing therethrough, and an aperture (10) communicating with the proximal end of the lumen. A tube (3) extends from the handle portion and has a tissue cutting device (7) located at the distal end of the tube. The handle includes first (11) and second (12) valves associated with the lumen of the handle portion, and the first and second tissue-pulling devices have shafts of a first diameter and second diameter respectively. The insert (19) comprises a stem (21) and a body portion (20), the stem being received in the aperture (10) to form a substantially gas-tight seal in combination with the first valve (11). The body portion (20) remains outside the aperture and includes a third valve (22), the third valve (22) being such that is forms a substantially gas-tight seal around the shaft of the second tissue pulling device (18) when the second tissue pulling device is inserted into the lumen of the insert.

17 Claims, 7 Drawing Sheets

(56) References Cited

U.S. PATENT DOCUMENTS

| | | | |
|---|---|---|---|
| 5,569,206 A | 10/1996 | Gorman, Jr. et al. | |
| 5,618,296 A * | 4/1997 | Sorensen et al. | 606/180 |
| 5,669,927 A * | 9/1997 | Boebel et al. | 606/180 |
| 5,713,869 A * | 2/1998 | Morejon | 604/174 |
| 6,039,748 A * | 3/2000 | Savage et al. | 606/180 |
| 6,068,603 A * | 5/2000 | Suzuki | 600/565 |
| 6,123,689 A | 9/2000 | To et al. | |
| 7,896,877 B2 | 3/2011 | Hall et al. | |
| 2002/0035372 A1 * | 3/2002 | Zisterer et al. | 606/180 |
| 2003/0225344 A1 * | 12/2003 | Miller | 600/568 |
| 2005/0070892 A1 * | 3/2005 | Ciarrocca | 606/46 |
| 2005/0261676 A1 * | 11/2005 | Hall et al. | 606/48 |
| 2005/0261677 A1 * | 11/2005 | Hall et al. | 606/48 |
| 2006/0047293 A1 * | 3/2006 | Haberland et al. | 606/167 |
| 2006/0253077 A1 * | 11/2006 | Smith | 604/167.06 |
| 2007/0219549 A1 * | 9/2007 | Marshall et al. | 606/34 |
| 2008/0039884 A1 * | 2/2008 | Nohilly et al. | 606/180 |
| 2008/0065021 A1 | 3/2008 | Jenkins et al. | |
| 2008/0065129 A1 * | 3/2008 | Batchelor et al. | 606/172 |
| 2008/0255597 A1 * | 10/2008 | Pravong et al. | 606/169 |
| 2009/0209915 A1 * | 8/2009 | Zastawny et al. | 604/167.02 |
| 2009/0292281 A1 * | 11/2009 | Fleming et al. | 606/48 |

FOREIGN PATENT DOCUMENTS

| | | |
|---|---|---|
| EP | 0 424 002 | 4/1991 |
| EP | 0 589 412 | 3/1994 |
| EP | 0 619 098 | 10/1994 |
| EP | 1 716 813 | 11/2006 |
| EP | 2 090 259 | 8/2009 |
| GB | 2 441 501 | 3/2008 |
| WO | WO 97/47248 | 12/1997 |
| WO | 2005/112806 | 12/2005 |
| WO | 2008/029092 | 3/2008 |

OTHER PUBLICATIONS

International Search Report for Application No. PCT/GB2011/000397, dated Jul. 5, 2011.

Written Opinion for Application No. PCT/GB2011/000397, dated Jul. 5, 2011.

* cited by examiner

FIG. 7

SURGICAL INSTRUMENT

CROSS-REFERENCE TO RELATED APPLICATIONS

This application claims priority from United Kingdom patent application number 1005437.7, filed 31 Mar. 2010.

TECHNICAL FIELD

This invention relates to a surgical instrument for use in a surgical intervention, most commonly in "keyhole" or minimally invasive surgery, but also in "open" surgery.

BACKGROUND TO THE INVENTION

Our published patent application WO2005/112806 describes a system for the morcellation of tissue in a minimally invasive procedure. Published patent application WO2008/029092 describes a valve mechanism for use in the morcellating instrument of the earlier application. This valve mechanism helps to ensure that an insufflating gas, used to expand the surgical site to allow for effective access, is constrained within the surgical site, even when a surgical instrument such as a tissue grasper is repeatedly inserted into and retracted from the morcellating instrument. The present invention provides an improvement to this type of arrangement, such that different types of surgical instrument, of different sizes, can be employed within the procedure while still maintaining the insufflating gas within the surgical site.

SUMMARY OF THE INVENTION

Accordingly, there is provided by one embodiment, in combination, a morcellator for morcellating tissue within a body, cavity of a patient, first and second tissue-pulling devices, and an insert;
the morcellator comprising
a handle portion having a lumen passing therethrough, the handle portion including an aperture communicating with the proximal end of the lumen,
a tube extending from the handle portion and being in communication with the lumen, the tube having a distal end,
a tissue cutting device located at the distal end of the tube and being capable of cutting tissue contacting the distal end of the tube, and
first and second valves associated with the lumen of the handle portion, the first valve being located in the region of the proximal end of the lumen, and the second valve being located more distally with respect to the first valve,
the first tissue pulling device having a shaft of a first diameter, and the second tissue pulling device having a shaft of a second diameter, the second diameter being less than the first diameter,
the second valve being such that it forms a substantially gas-tight seal when no tissue pulling device is inserted within the handle, and the first valve being such that it forms a substantially gas-tight seal around the shaft of the first tissue pulling device when the first tissue pulling device is inserted within the handle, but that it does not form a substantially gas-tight seal around the shaft of the second tissue pulling device when the second tissue pulling device is inserted within the handle,
the insert comprising a stem and a body portion;
the stem including a lumen and being of a size such that it can be received in the aperture in the handle to locate the insert against the handle and form a substantially gas-tight seal in combination with the first valve, the stem being of such a length that it does not extend into the handle as far as the second valve,
the body portion remaining outside the aperture and including a third valve, the third valve being such that it forms a substantially gas-tight seal around the shaft of the second tissue pulling device when the second tissue pulling device is inserted into the lumen of the insert.

The insert allows smaller diameter instruments, such as the second tissue pulling device, to be used while still maintaining a substantially gas-tight seal around the shaft thereof. This is something that the first valve is unable to manage effectively, as it is designed to form a substantially gas-tight seal with the larger diameter shaft of the first tissue pulling device. This combination allows the user of the surgical system to use either the first or second tissue pulling devices, or even both devices alternately, while still maintaining an effective seal for the insufflating gas.

The insert is designed such that it is received in the first valve, but does not extend as far as the second valve. Accordingly, the stem of the insert preferably has a length less than 75 mm, conveniently less than 50 mm, and typically less than 25 mm. In this way the stem is sufficient to be received through the first valve, forming a substantially gas-tight seal therewith, but is not so long as to penetrate the second valve, as this could cause leakage of insufflation gas when the insert is in place but no tissue grasping instrument is present within the insert.

According to one convenient arrangement, the third valve is such that it does not form a substantially gas-tight seal when no tissue pulling device is inserted within the handle. This is because it is not necessary for the third valve to seal the surgical site when no tissue grasping device is present, as this is the function of the second valve. Accordingly, the third valve conveniently includes an aperture having a diameter of less than 5 mm. This provides for easy introduction of the second tissue grasping device, which can either be introduced into the insert once the insert has been located on the morcellator handle, or alternatively, the insert can be located on the second tissue grasping device, and the insert and second tissue grasping device can be introduced into the morcellator handle in combination.

The stem of the insert is preferably provided with one or more ribs adapted to cooperate with the first valve in order to retain the insert within the handle. The ribs ensure that the insert does not become detached from the morcellator handle every time that the second tissue pulling device is removed from the morcellator. Accordingly, the insert is preferably such that it will remain attached to the handle when subjected to a force within a first predetermined range, typically less than 7 Newtons. Conversely, the insert is preferably such that it can be detached when desired, or in circumstances in which the insert remaining attached to the morcellator handle would cause an obstruction or blockage. Accordingly, the insert is preferably such that it will become detached from the handle when subjected to a force within a second predetermined range, typically greater than 10 Newtons.

The one or more ribs may conveniently be in the form of a screw thread provided on the stem. As an alternative to ribs, the diameter of the stem may conceivably vary over its length so as to provide a variable interference fit between the stem of the insert and the handle.

In one convenient arrangement, the second tissue pulling device includes a shaft having a certain diameter, and a pair of jaws, the jaws being movable between a closed position in which the jaws lie within the diameter of the shaft, and a range of open positions at least some of which are such that the jaws extend beyond the diameter of the shaft. In these circumstances the arrangement is conveniently such that the insert remains attached to the handle when the second tissue pulling device is withdrawn with its jaws in the closed position. Similarly, the arrangement is conveniently such that the insert remains attached to the handle when the second tissue pulling device is withdrawn with its jaws in the open position but still within the diameter of the shaft. However, when the second tissue pulling device is withdrawn with its jaws open such that they extend beyond the diameter of the shaft, they are likely to contact the insert and the tissue pulling device is likely to become stuck within the morcellator if the insert remains attached. Consequently, the arrangement is such that the insert becomes detached from the handle when the second tissue pulling device is withdrawn with its jaws in the open position and extending beyond the diameter of the shaft.

Although the combination has been described above as a tissue morcellating device receiving one or more tissue grasping devices, the inventive concept of the present invention extends beyond such arrangements to other combinations of surgical equipment. Accordingly, in one embodiment the invention also resides in a combination of a surgical access device capable of sequentially receiving at least first and second surgical instruments having shafts of differing diameters, and an insert;

the surgical access device comprising
a body portion having a lumen passing therethrough, the body portion including an aperture communicating with the proximal end of the lumen, and
a valve associated with the lumen of the body portion,
the valve being such that it is capable of forming a substantially gas-tight seal around the shaft of a surgical instrument insertable within the handle, provided the diameter of the shaft is within a first prescribed range, but that the valve is not capable of forming a substantially gas-tight seal around the shaft when the diameter of the shaft is below the prescribed range,
the insert comprising a stem and a body portion,
the stem including a lumen and being of a size such that it can be received in the aperture in the body portion to locate the insert against the surgical access device, the stem being of a length less than 75 mm,
the body portion remaining outside the aperture and including a further valve, the further valve being such that it is capable of forming a substantially gas-tight seal around the shaft of a surgical instrument insertable within the handle, when the diameter of the shaft is in a second prescribed range, the second prescribed range including diameters smaller than those in the first prescribed range.

Typically, the surgical access device can comprise a tissue morcellator as previously described, or, alternatively a port or trocar commonly used in minimally invasive surgery to introduce surgical instruments to a surgical site. By the term "surgical instrument", there is meant to include tissue grasping devices as previously described, but also visualization devices such as endoscopic cameras, tissue treatment instruments such as electrosurgical instruments capable of the coagulation or vaporization of tissue, mechanical instruments capable of manipulating tissue, suction devices or other tissue capture devices such as biopsy devices or stone removal devices. The term "surgical instrument" includes any instrument capable of assisting in a minimally invasive surgical procedure.

Similarly, the invention also resides, according to one embodiment thereof, in the combination of a surgical access device, first and second surgical instruments, and an insert;

the surgical access device comprising
a body having a lumen passing therethrough, the body portion including an aperture communicating with the proximal end of the lumen, and
a valve associated with the lumen of the body portion,
the first surgical instrument having a shaft of a first diameter, and the second surgical instrument having a shaft of a second diameter, the second diameter being less than the first diameter,
the valve being, such that it forms a substantially gas-tight seal around the shaft of the first surgical instrument when the first surgical instrument is inserted within the body portion, but that it does not form a substantially gas-tight seal around the shaft of the second surgical instrument when the second surgical instrument is inserted within the body portion,
the insert comprising a stem and a body portion,
the stem including a lumen and being of a size such that it can be received in the aperture in the body portion to locate the insert against the surgical access device, the stem being of a length less than 75 mm,
the body portion remaining outside the aperture and including a further valve, the further valve being such that is forms a substantially gas-tight seal around the shaft of the second surgical instrument when the second surgical instrument is, inserted within the surgical access device.

BRIEF DESCRIPTION OF THE DRAWINGS

Embodiments of the invention will now be further described, by way of example only, with reference to the accompanying drawings, in which.

DESCRIPTION OF THE EMBODIMENTS

Figure 1:
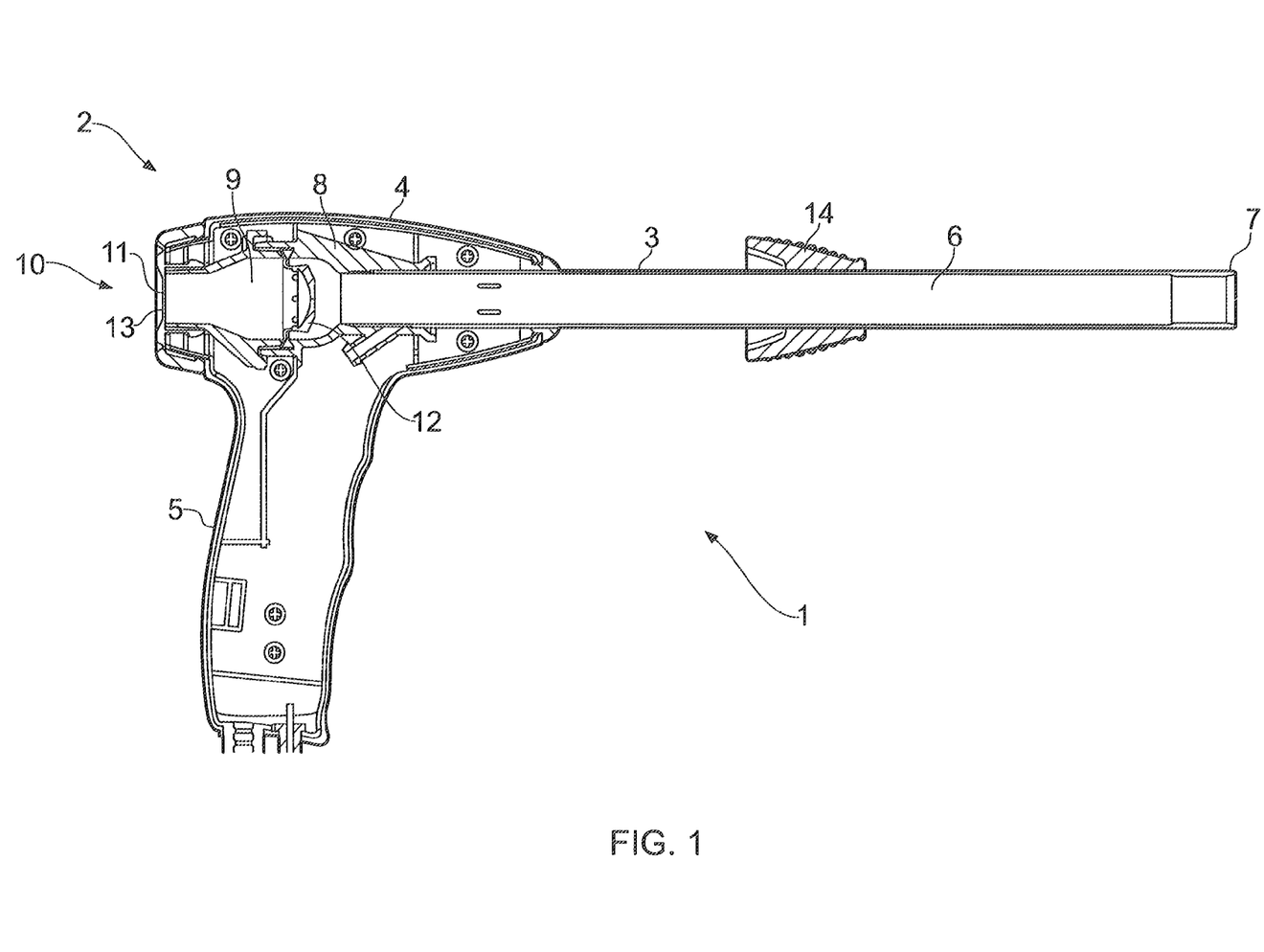
FIG. 1 is a schematic sectional side view of a morcellating device forming part of an embodiment of the present invention.

Referring to the drawings, FIG. 1 shows a morcellating device shown generally at 1, comprising a plastics handle 2 and a tubular shaft 3. The handle 2 comprises an upper part 4 from which the tubular shaft 3 extends, and a lower part 5 constituting a grip portion by which the morcellating device can be held by a user. The tubular shaft 3 is hollow, and defines a lumen 6 therein. The distal end of the shaft is provided with an electrosurgical electrode assembly 7, as described in our published patent application WO05/112806, which was also published as US 2005/0261677 A1, now U.S. Pat. No. 7,896, 877, the entire contents of each of which are hereby incorporated by way of reference.

The proximal end of the tubular shaft 3 is located within a support 8 forming part of the upper part 4 of the handle 2. The upper part of the handle 2 is hollow; defining a chamber 9 in communication with the lumen 6. The upper part 4 is also provided with an aperture 10. The aperture 10 is in communication with the chamber 9 and, together with the lumen 6, forms an axial passageway from the aperture 10 to the distal end of the shaft 3.

A first valve 11 is present across the aperture 10, and a second valve 12 is located within the chamber 9 at a distance of some 85 mm from the first valve 11. The first valve 11 has a central aperture 13, typically 8 mm in, diameter. The second valve is of a design described in our patent application WO08/029,092, which was also published as US 2008/0065021 A1, the entire contents of both of which are also hereby incorporated by way of reference.

In use, the morcellating device 1 is inserted into the abdomen of a patient, either through a direct incision in the abdomen or using a port or trocar (not shown). A depth stop 14 is located, on the shaft 3 in order to assist in setting the depth to which the device 1 is inserted. The abdomen of the patient is insufflated with a gas (typically carbon dioxide) to expand the abdomen, the valve 12 preventing the escape of gas through the morcellating device 1. The device 1 is connected to an electrosurgical generator (not shown) to power the electrosurgical electrode assembly 7, in order that tissue brought into contact with the distal end of the shaft is electrosurgically cut.

Figure 2:
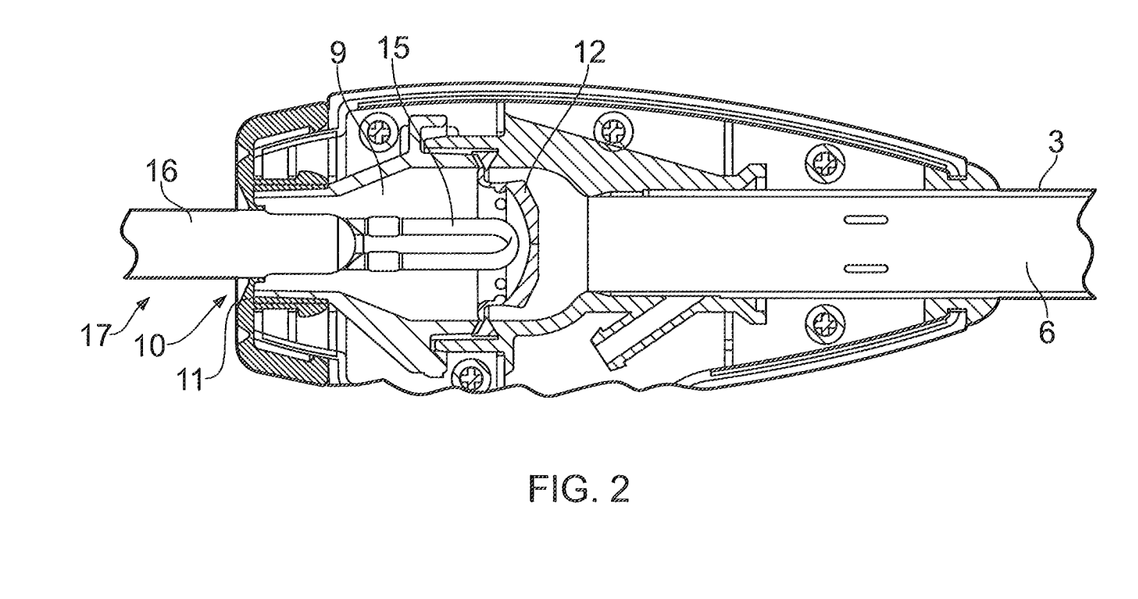
FIG. 2 is a sectional side view of part of the morcellating device of FIG. 1, in combination with a first grasping instrument.

The device 1 is normally operated in conjunction with one or more tissue graspers, as will now be described in more detail. A typical tissue grasper is described in patent application WO2005/112806, and includes a pair of jaws 15 mounted on a shaft 16, and opened and closed by a scissor-type handle arrangement (not shown). A first tissue grasper 17 is shown in FIG. 2, with only the tip of the grasper being shown entering the morcellating device 1. The shaft 16 of the first tissue grasper is approx 10 mm in diameter, so that the shaft forms an effective gas-tight seal with the first valve 11 when the tissue grasper 17 is inserted into the chamber 9. As the tissue grasper 17 is inserted further into the morcellating device, it extends through the valve 12 and eventually protrudes from the distal end of the tubular shaft 3.

The surgeon manoeuvres the tissue grasper 17 to grasp tissue between the jaws 15, and pulls the tissue against the distal end of the tubular shaft 3 and into contact with the electrosurgical electrode assembly 7. The electrode assembly severs the tissue and allows a slug of tissue to be, pulled through the lumen 6 and out of the morcellating device through the aperture 10. This process can be repeated to achieve bulk tissue removal, as described in full detail in WO2005/112806.

Figures 3, 3A:
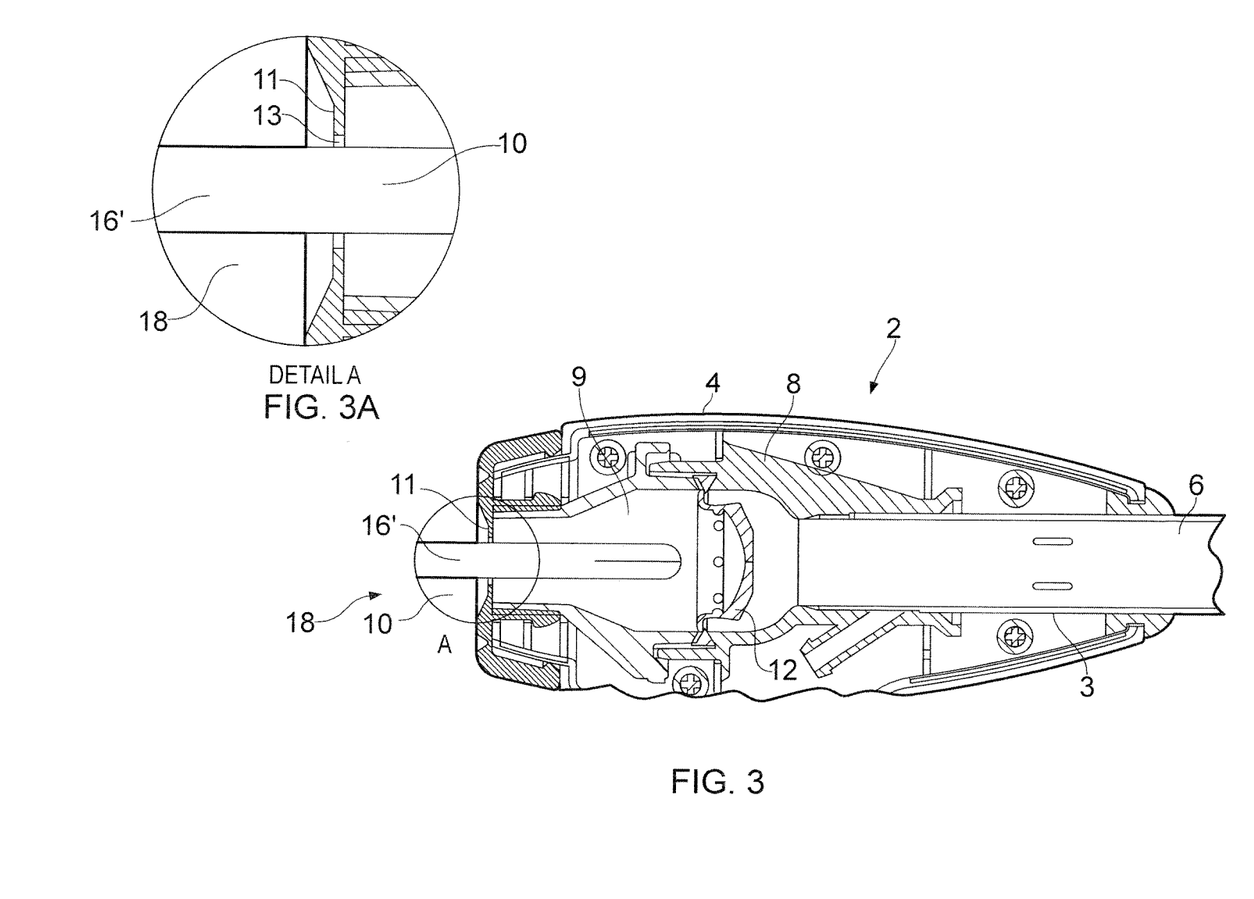
FIG. 3 is, a sectional side view of part of the morcellating device of FIG. 1, in combination with a second grasping instrument.
FIG. 3A is an enlarged view of part of FIG. 3.

The first tissue grasper 17 is a 10 mm tissue grasper. However, it is sometimes necessary to use a smaller instrument, such as a second tissue grasper 18 as shown in FIG. 3. Tissue grasper 18 has a shaft 16' with a diameter of 5 mm, and is accordingly known as a 5 mm tissue grasper. The problem with this arrangement is that, as shown in FIG. 3A, the smaller diameter shaft 16' of the second tissue grasper 18 fails to make a gas-tight seal with the first valve 11. The second valve 12 forms a gas-tight seal when there is no tissue grasper present, but does not form a gas-tight seal when the shaft 16" of the second tissue grasper 18 passes through the valve 12. In this way, gas can leak from the surgical patient, and the insufflation pressure can fall, causing problems during the surgical procedure.

Figure 4:
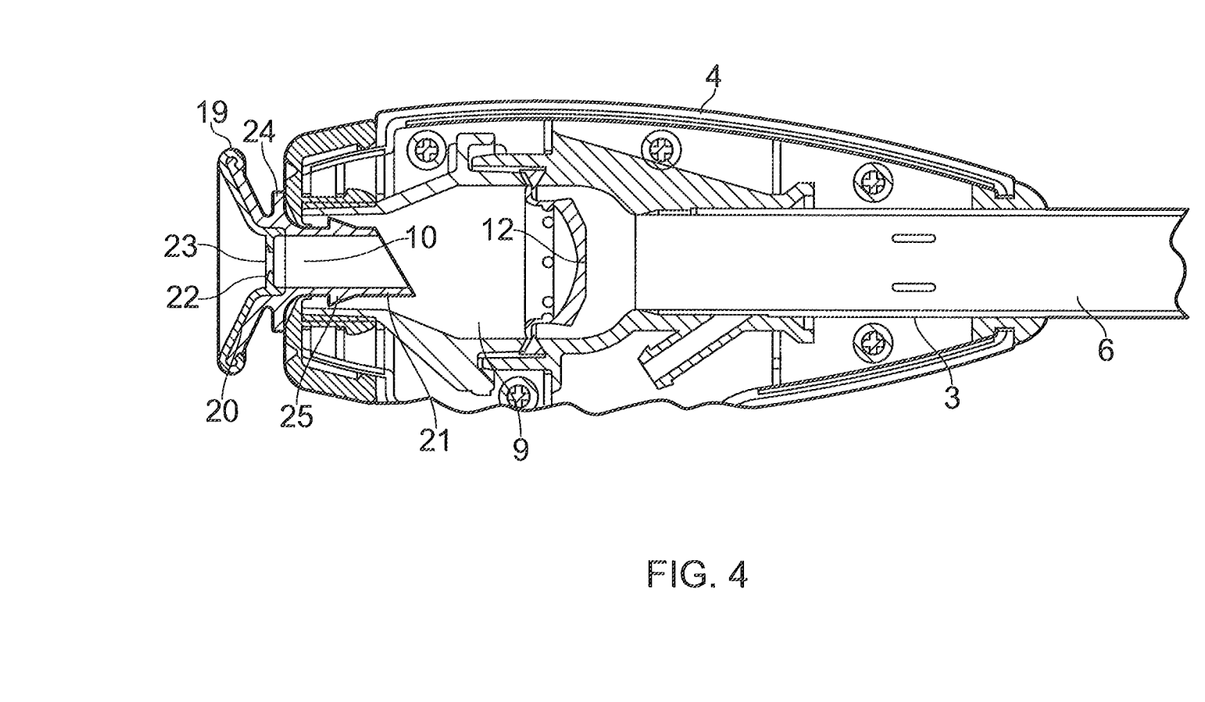
FIG. 4 is a sectional side view of part of the morcellating device of FIG. 1, in, combination with an insert forming part of an embodiment of the present invention.

The central aperture 13 in the first valve 11 cannot be made sufficiently small so as to form a gas tight seal with the 5 min tissue grasper 18 without causing difficulties in inserting and manoeuvring the 10 mm tissue grasper 17. However, this problem is overcome by the use of an insert 19, as shown in FIG. 4. The insert 19 comprises a conical body portion 20, and a short tubular stem 21 extending therefrom. The body portion 20 is provided with a third valve 22, extending across the entrance portion and having a central aperture 23, typically of around 3 or 4 mm in diameter.

Figure 5:
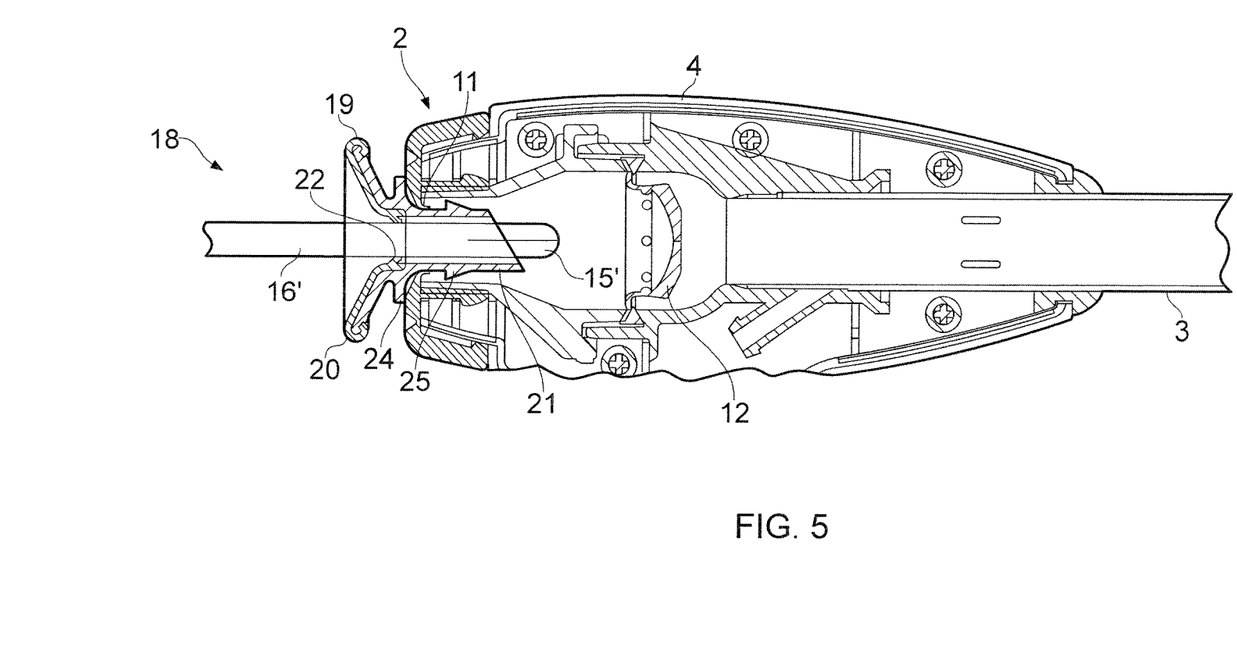
FIG. 5 is a sectional side view of part of the morcellating device of FIG. 1, in combination with the insert of FIG. 4 and the second grasping instrument of FIG. 3.

In use, the insert is presented to the morcellating device 1, and the stem 21 is inserted in the aperture 10 through the first valve 11. The insert 19 has a flange 24 designed to abut the handle 2 adjacent the aperture 10, and a rib 25 present on the stem 21 designed to prevent inadvertent removal of the insert from the handle 2. As shown in FIG. 5, the second tissue grasper 18 is inserted through the insert 19, the first valve 11 forms a substantially gas-tight seal with the stem 21 of the insert, and the third valve 22 forms a substantially gas-tight seal against the shaft 16' of the tissue grasper 18. In this way, no insufflation pressure is lost when the morcellating device 1 is used with a 5 mm grasper, such as the grasper 18.

As described above, the insert 19 is located on the morcellating device 1, and the grasper 18 is then inserted through the insert 19. Alternatively, the insert 19 can firstly be located on the tissue grasper 18, and the combination of insert and tissue grasper can then be inserted into the morcellating, device 1. This method chosen will depend upon the preference of the individual surgeon.

The tissue grasper 18 will normally be inserted and withdrawn several times during a morcellation procedure, as tissue is grasped, cut and removed from the patient. When the grasper is retracted with its jaws 15' in a closed position, the grasper will normally be removable through the insert 19 leaving the insert in situ, still attached to the morcellating device 1. This is the situation shown in FIG. 5, and will be the case even if the jaws are grasping, tissue, provided the amount of tissue grasped is not too great to pass through the hollow stem 21.

Figure 6:
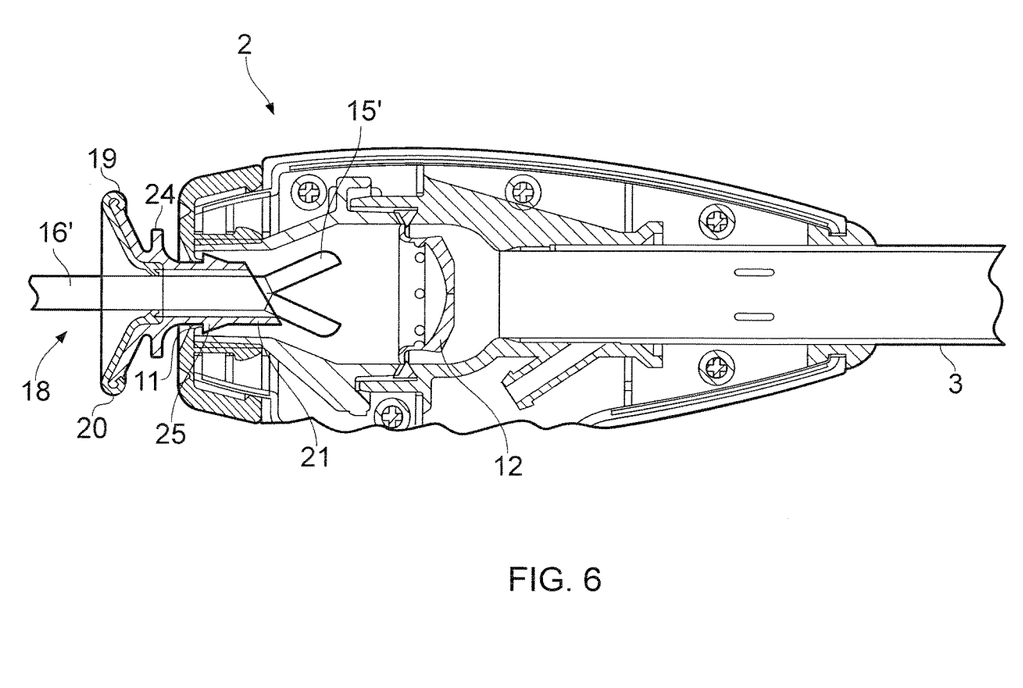
FIG. 6 is a sectional side view of the combination of FIG. 5, shown with the grasping instrument in an open-jawed position.
Figure 7:
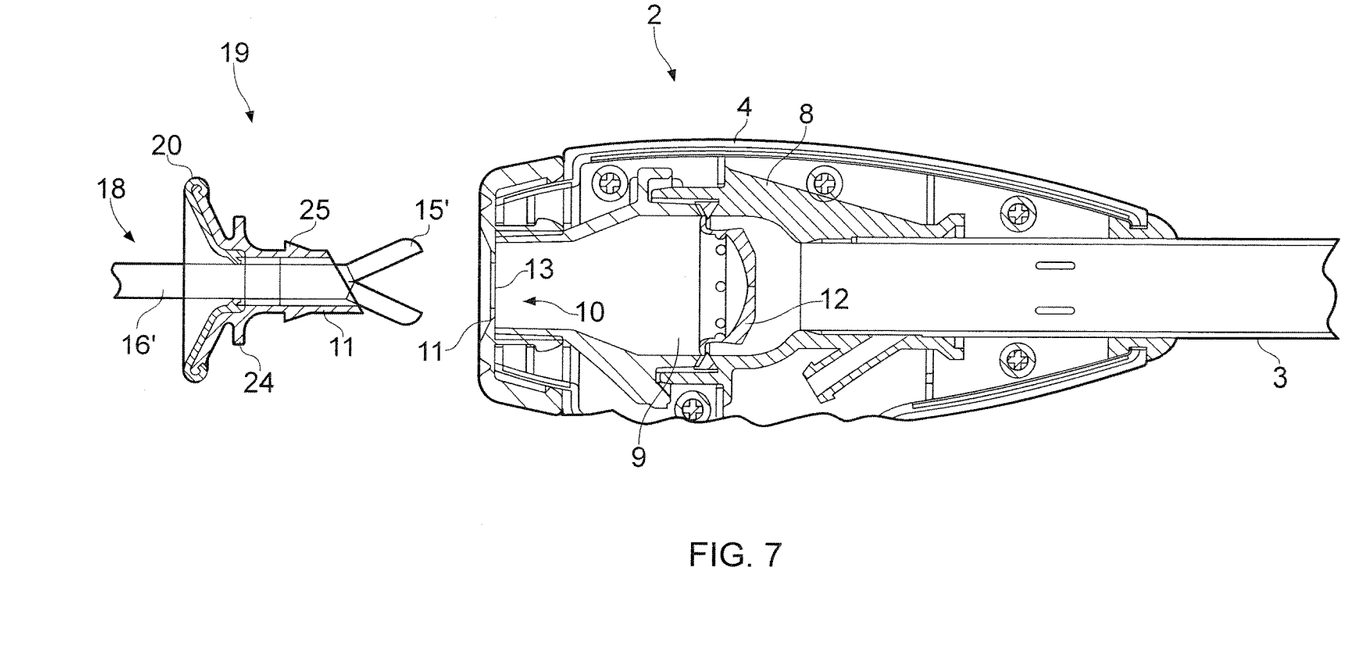
FIG. 7 is a sectional side view of the combination of FIG. 6, shown with the insert and grasping instrument detached from the morcellating device.

FIG. 6 shows the position where the surgeon is attempting to withdraw the tissue grasper 18 with the jaws 15' in their open position, or with so much tissue grasped between the jaws that they are unable to close properly. In this situation the jaws 15' engage against the end of the stem 21 as the grasper is retracted, and cause the insert 19 to be removed from the handle 2, as shown in FIG. 7. The rib 25 assists in setting the force needed to cause the insert 19 to become detached from the handle 2, a force of typically 10 Newtons being required to overcome the engagement of the rib 25 against the valve 11.

The insert 19 is different from a conventional 5 mm port device. Firstly, it has an aperture 23 in the valve 22, a feature not normally present on a 5 mm port. Secondly, the length of the stem 21 is much shorter than that normally present on a 5 mm port. The stem 21 of the insert 19 is typically less than 25 mm in length, whereas typical 5 mm ports are much longer. The length of the stem 21 is such that, even when fully inserted in the handle 2, it does not extend so far as to protrude through the second valve 12.

Embodiments of the invention have been described above in the context of a morcellating device in combination with tissue grasping instruments. However, it will be appreciated that the principles of embodiments of the invention can be deployed in any situation in which a surgical access device is used in combination with different sized devices or instruments. Examples of surgical access devices include ports and trocars in addition to morcellators. Similarly, devices other than tissue graspers include visualization devices such as endoscopic cameras, tissue manipulating or retrieval instruments, suction or irrigation instruments, or electrosurgical instruments capable of the coagulation, vaporization or dissection of tissue.

The invention claimed is:

1. In combination, a morcellator for morcellating tissue within a body cavity of a patient, first and second tissue-pulling devices, and an insert; the morcellator comprising;
 a handle portion having a lumen passing therethrough, the handle portion including an aperture communicating with the proximal end of the lumen,
 a tube extending from the handle portion and being in communication with the lumen, the tube having a distal end,
 a tissue cutting device located at the distal end of the tube and being capable of cutting tissue contacting the distal end of the tube, and
 first and second valves associated with the lumen of the handle portion, the first valve being located in the region of the proximal end of the lumen, and the second valve being located more distally with respect to the first valve,
 the first tissue pulling device having a shaft of a first diameter, and the second tissue pulling device having a shaft of a second diameter, the second diameter being less than the first diameter,
 the second valve being such that it forms a substantially gas-tight seal when no tissue pulling device is inserted within the handle, and the first valve being such that it forms a substantially gas-tight seal around the shaft of the first tissue pulling device when the first tissue pulling device is inserted within the handle, but that it does not form a substantially gas-fight seal around the shaft of the second tissue pulling device when the second tissue pulling device is inserted within the handle,
 the insert comprising a stem and a body portion,
 the stem including a lumen and being of a size such that it can be received in the aperture in the handle to locate the insert against the handle and form a substantially gas-tight seal in combination with the first valve, the stem being received within the first valve and receipt of the stem within the first valve being the sole method of attachment between the insert and the handle and being of such a length that it does not extend into the handle as far as the second valve,
 the body portion remaining outside the aperture and including a third valve, the third valve being such that it forms a substantially gas-tight seal around the shaft of the second tissue pulling device when the second tissue pulling device is inserted into the lumen of the insert.

2. The combination according to claim 1, wherein the stem of the insert has a length less than 75 mm.

3. The combination according to claim 2, wherein the stem of the insert has a length less than 50 mm.

4. The combination according to claim 3, wherein the stem of the insert has a length less than 25 mm.

5. The combination according to claim 1, wherein the third valve is such that it does not form a substantially gas-tight seal when no tissue pulling device is inserted within the handle.

6. The combination according to claim 5, wherein the third valve includes an aperture having a diameter of less than 5 mm.

7. The combination according to claim 1, wherein the stem of the insert is provided with one or more ribs adapted to cooperate with the first valve in order to retain the insert within the handle.

8. The combination according to claim 1, wherein the insert is such that it will remain attached to the handle when subjected to a force within a first predetermined range.

9. The combination according to claim 8, wherein the first predetermined range is less than 7 Newtons.

10. The combination according to claim 1, wherein the insert is such that it will become detached from the handle when subjected to a force within a second predetermined range.

11. The combination according to claim 10, wherein the second predetermined range is greater than 10 Newtons.

12. The combination according to claim 1, wherein at least the second tissue pulling device includes a shaft having a certain diameter, and a pair of jaws, the jaws being movable between a closed position in which the jaws lie within the diameter of the shaft, and a range of open positions at least some of which are such that the jaws extend beyond the diameter of the shaft.

13. The combination according to claim 12, wherein the arrangement is such that the insert remains attached to the handle when the second tissue pulling device is withdrawn with its jaws in the closed position.

14. The combination according to claim 12, wherein the arrangement is such that the insert remains attached to the handle when the second tissue pulling device is withdrawn with its jaws in the open position but still within the diameter of the shaft.

15. The combination according to claim 12, wherein the arrangement is such that the insert becomes detached from the handle when the second tissue pulling device is withdrawn with its jaws in the open position and extending beyond the diameter of the shaft.

16. In combination, a surgical access device capable of sequentially receiving at least first and second surgical instruments having shafts of differing diameters, and an insert; the surgical access device comprising;
 a body portion having a lumen passing therethrough, the body portion including an aperture communicating with the proximal end of the lumen, and
 a valve associated with the lumen of the body portion,
 the valve being such that it is capable of forming a substantially gas-tight seal around the shaft of a surgical instrument insertable within the handle, provided the diameter of the shaft is within a first prescribed range, but that the valve is not capable of forming a substantially gas-tight seal around the shaft when the diameter of the shaft is below the prescribed range,
 the insert comprising a stem and an insert body portion,
 the stem including a lumen and being of a size such that it can be received in the aperture in the body portion to locate the insert against the surgical access device, the stem being of a length less than 75 mm and being received within the valve and receipt of the stem within the valve being the sole method of attachment between the insert and the surgical access device,
 the insert body portion remaining outside the aperture and including a further valve, the further valve being such that it is capable of forming a substantially gas-tight seal around the shaft of a surgical instrument insertable within the handle, when the diameter of the shaft is in a second prescribed range, the second prescribed range including diameters smaller than those in the first prescribed range.

17. In combination, a surgical access device, first and second surgical instruments, and an insert; the surgical access device comprising:

a body portion having a lumen passing therethrough, the body portion including an aperture communicating with the proximal end of the lumen, and a valve associated with the lumen of the body portion, the first surgical instrument having a shaft of a first diameter, and the second surgical instrument having a shaft of a second diameter, the second diameter being less than the first diameter, the valve being such that it forms a substantially gas-tight seal around the shaft of the first surgical instrument when the first surgical instrument is inserted within the body portion, but that it does not form a substantially gas-tight seal around the shaft of the second surgical instrument when the second surgical instrument is inserted within the body portion, the insert comprising a stem and an insert body portion, the stem including a lumen and being of a size such that it can be received in the aperture in the body portion to locate the insert against the surgical access device, the stem being of a length less than 75 mm and being received within the valve and receipt of the stem within the valve being the sole method of attachment between the insert and the surgical access device, the insert body portion remaining outside the aperture and including a further valve, the further valve being such that is forms a substantially gas-tight seal around the shaft of the second surgical instrument when the second surgical instrument is inserted within the surgical access device.

* * * * *